United States Patent
Ballestrazzi et al.

(10) Patent No.: US 6,843,359 B2
(45) Date of Patent: Jan. 18, 2005

(54) AUTOMATIC FEED DEVICE FOR INDIVIDUAL PUBLISHING PRODUCTS

(75) Inventors: Aris Ballestrazzi, Savignano sul Panaro (IT); Lamberto Tassi, Savignano sul Panaro (IT)

(73) Assignee: Sitma S.p.A., Spilamberto - Modena (IT)

( * ) Notice: Subject to any disclaimer, the term of this patent is extended or adjusted under 35 U.S.C. 154(b) by 0 days.

(21) Appl. No.: 10/376,995

(22) Filed: Feb. 28, 2003

(65) Prior Publication Data

US 2003/0168315 A1 Sep. 11, 2003

(30) Foreign Application Priority Data

Mar. 6, 2002 (IT) ...................................... MI2002A0460

(51) Int. Cl.⁷ .......................... B65G 47/30; B65H 5/16; B65H 3/08; B65H 5/00
(52) U.S. Cl. ............... 198/418.6; 198/471.1; 271/91; 271/107; 271/225
(58) Field of Search ........................... 198/418.6, 471.1, 198/469.1, 470.1, 477.1; 271/90, 91, 93, 107, 225

(56) References Cited

U.S. PATENT DOCUMENTS

| | | | | |
|---|---|---|---|---|
| 5,308,055 A | * | 5/1994 | Binnen ........................ | 271/107 |
| 5,901,530 A | * | 5/1999 | Draghetti et al. ......... | 198/471.1 |
| 5,921,375 A | * | 7/1999 | van Laar .................. | 198/471.1 |
| 6,098,785 A | * | 8/2000 | Van Maanen ............ | 198/459.8 |
| 6,386,812 B2 | * | 5/2002 | Garlichs et al. .......... | 198/471.1 |

* cited by examiner

*Primary Examiner*—Gene O. Crawford
(74) *Attorney, Agent, or Firm*—Hedman & Costigan, P.C.

(57) ABSTRACT

An automatic feed device for individual publishing products of different thickness and sizes includes a first conveyor belt (13) and a second conveyor belt (14) arranged with the first conveyor belt (13) being partially over the second conveyor belt (14) in combination with an automatic feed device having a bearing structure (15), a pair of manipulator members (19) for gripping the publishing products (12) on the first conveyor belt (13). The publishing products are then laid down on the second conveyor belt (14) separate from one another while the manipulators (19) alternately move forwards and backwards between the first and second conveyor belt (13, 14) to transfer the individual publishing products to two predetermined positions on the first and second conveyor belts (13, 14).

10 Claims, 3 Drawing Sheets

AUTOMATIC FEED DEVICE FOR INDIVIDUAL PUBLISHING PRODUCTS

Figure 1:
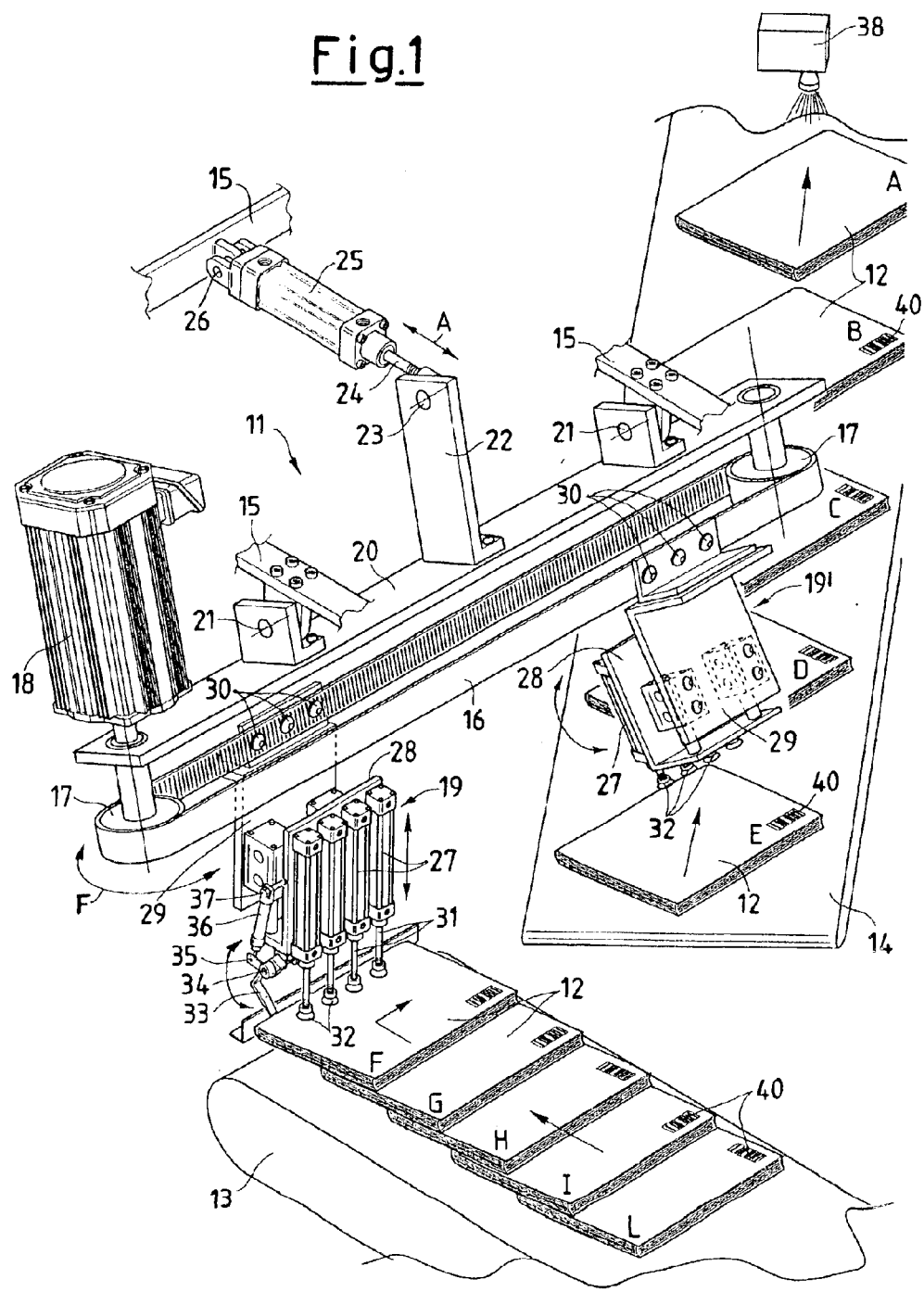

The present invention refers to an automatic feed device for individual publishing products, in particular for publishing products of whatever thickness and size.

Once the "publishing products", such as newspapers, magazines, books, with or without gadgets, bound in plastic or not, and the like, have been distributed according to the predetermined program, they are returned in the leftover amount, in bulk, to sorting centres. These centres must take care of their selection for counting, selection and whatever else is required so as to reuse the materials and to have information on the size of the distribution as well as where they come from.

In general, these returned products, arrive at such centres, where suitable personel select them coming out from their containers to divide them and to allow their type and origin to be checked.

In such a way, there are costs due to the substantial use of personnel needed to carry out such a task, which moreover does not manage to maintain fast selection and sending of the individual product towards the selection and checking devices.

Moreover, the variability of their size and thickness does not always make this operation easy with a further slowing down of the relative operations and consequent increase in the costs.

Therefore, it is the general purpose of the present invention to identify and realise an automatic feed device for individual publishing products which solves such a technical problem so as to have easy and always correct automatic separation of publishing products, as required.

Another purpose is that of realising a feed device which can be directly associated with a transporter for feeding products which are arranged overlapping with end edges above the next product, avoiding any type of manipulation by personnel.

Yet another purpose is that of identifying a device which makes the carrying out of the selection, sorting and type and origin check operations of leftover publishing products as automatic and fast as possible.

Yet another purpose is that of realising an automatic feed device for individual publishing products which can easily function irrespective of the size and thickness of the leftover products which arrive arranged scaled on a conveyor belt.

These and other purposes according to the present invention are achieved by realising an automatic feed device for individual publishing products as outlined in claim 1 attached hereto.

Further relevant characteristics of the present invention are object of the dependent claims.

Through a device according to the present invention an automatic arrangement of the publishing products separated one after the next on a discharge conveyor belt which sends them to subsequent selection, sorting and type and origin check operations of leftover publishing products is thus achieved.

It must be noted that such a device can quickly be adapted to selection lines already present at the centres which receive the leftover products and select them for them to be recycled.

Figure 2:
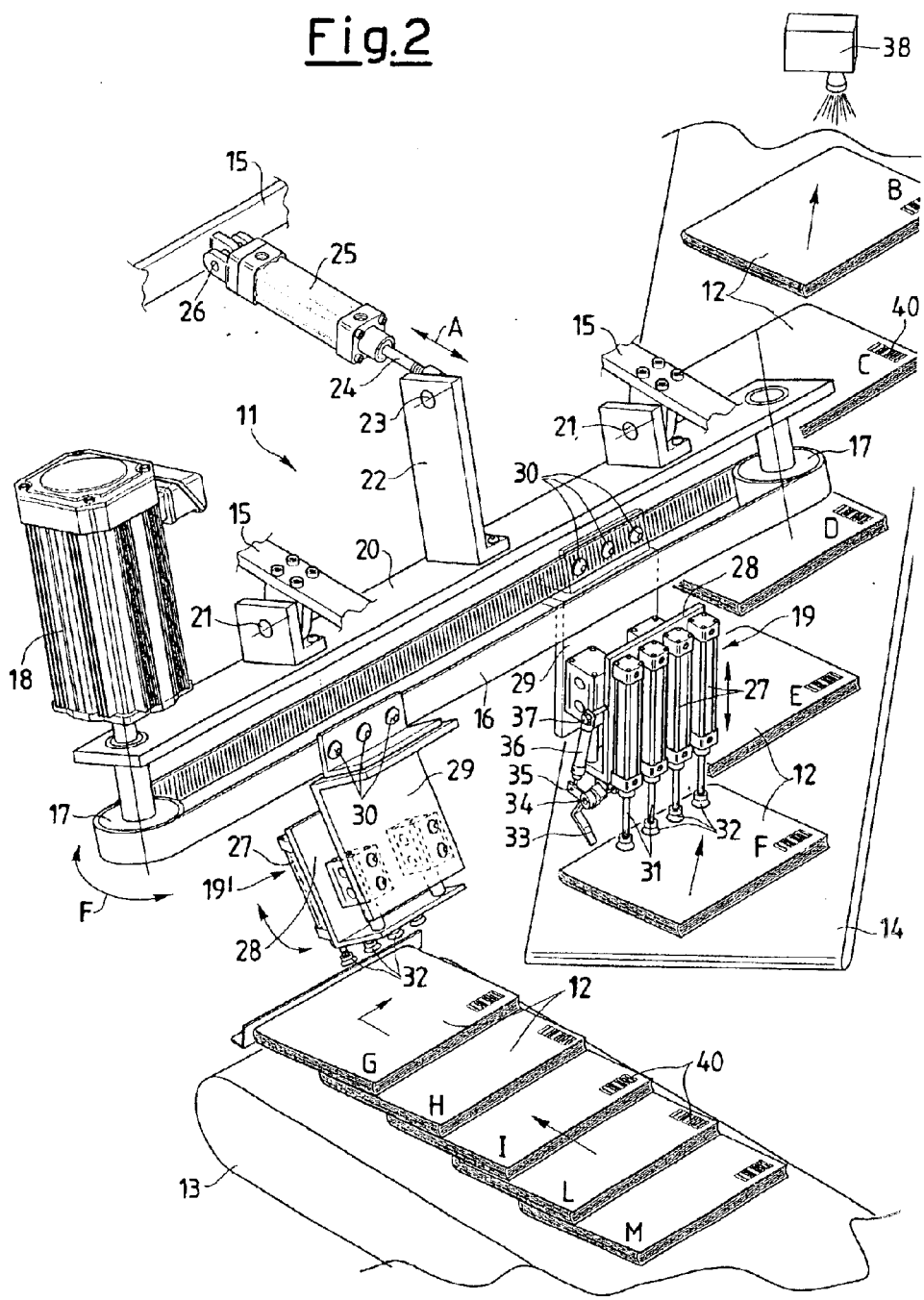
Figure 3:
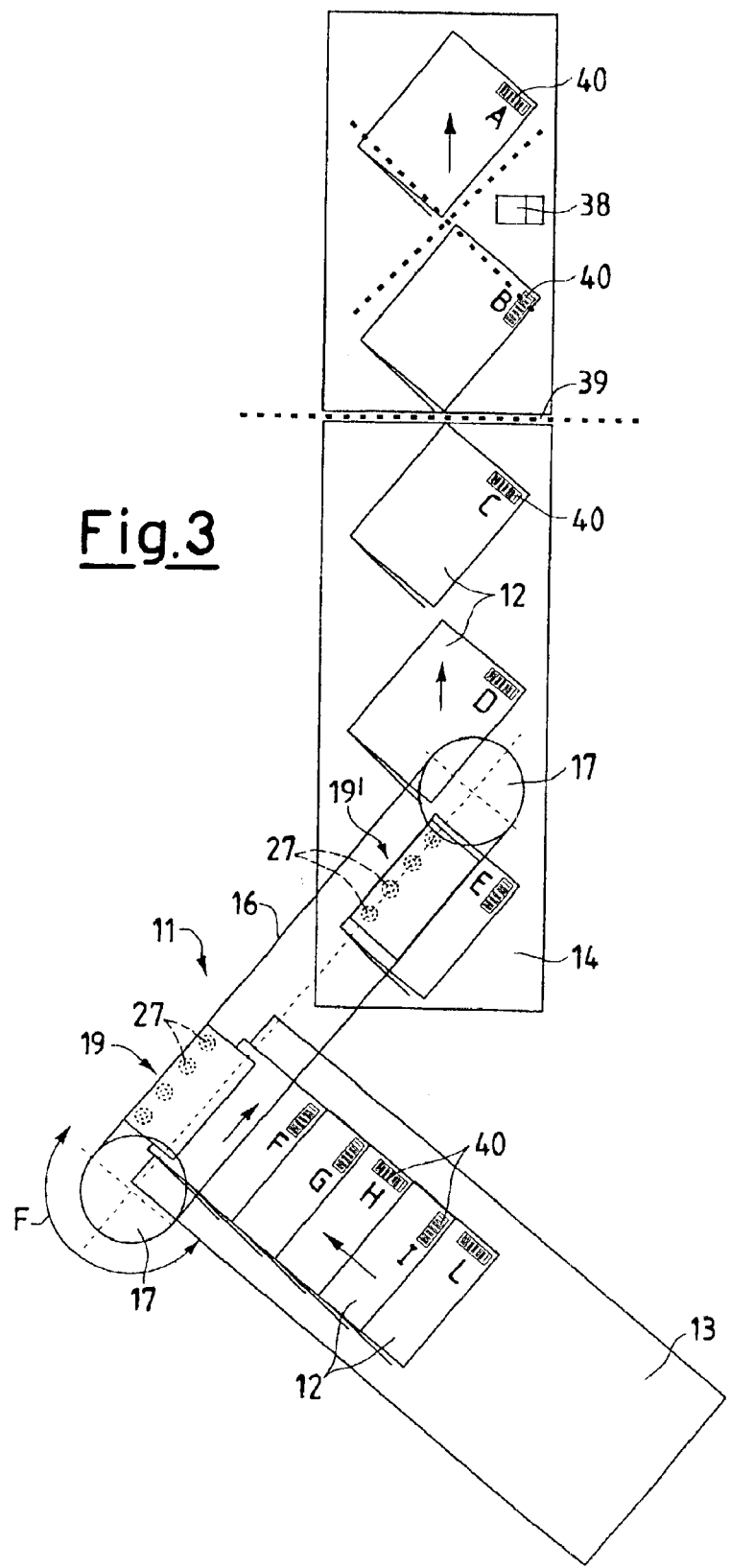

The functional and structural characteristics and the advantages of a device according to the invention shall become clearer from the description of a non-limiting example embodiment thereof, with reference to the attached drawings, in which:

FIG. 1 schematically shows a perspective view of an automatic feed device for individual publishing products arranged between a first conveyor belt for feeding in a scaled arrangement of them, one partially on top of the next, and a second conveyor belt which receives them one after the next separated and not overlapping, FIG. 2 is a view similar to that of FIG. 1 in which the device is releasing a product onto the second conveyor belt, FIG. 3 is a totally schematic plan view of another position of the device.

With reference to the drawings, an automatic feed device for individual publishing products according to the present invention is shown, wholly indicated with 11, to which publishing products 12, of whatever thickness and size, are fed. These products are taken from a first feed conveyor belt 13 in an scaled arrangement, one partially on top of the other and indicated both with 12 and in order through letters of the alphabet F, G, H, I, L, M, etc., said "negative squama" arrangement, in other words with the rear edge of a first product arranged above the front edge of a second product.

The feeder device of the present invention automatically picks up the individual publishing products 12 and places them individually on a second conveyor belt 14, one after the other separated and not overlapping, indicated with both 12 and with letters of the alphabet A, B, C, D, E, F.

As stated previously, by the term "publishing product" we mean a packaged or unpackaged product, alone or a composite with a variable size and thickness. Indeed, with the base product, such as a newspaper, a magazine, a book or the like, it is possible to combine at least one second product, of the same or a different size which functions as an additional element, such as some sort of "gadget", a compact disc, a floppy disc, a perfume or any other object which is sufficiently small.

The device of the invention thus arranged comprises a bearing structure, schematised at 15, on which a belt 16 is arranged, wound into a ring on end pulleys 17. One of these pulleys 17 is commanded by a brushless motor 18 or by an "electric shaft" group which commands the pulley in an alternating backward and forward motion, with the possibility of previously selecting accelerating, continuous and decelerating movement. In this way an arrangement with an actuator, which moves at least one pair of manipulator members, indicated with 19, 19', backwards and forwards, is realised.

The belt 16, indeed, in the example carries two manipulators 19, 19' which grip one at a time the publishing products 12 which, as stated, are arranged scaled and advance on the first conveyor belt 13. Once the products 12 are gripped they are displaced by the belt 16 and taken above the second conveyor belt 14, where they are laid down. In particular, the publishing products 12 are laid down separated from each other, as shown in the figures.

In such a way the manipulators 19, 19' are alternately mobile forwards and backwards between the first conveyor belt 13 and the second conveyor belt 14. Moreover, it must be noted that the pulleys 17, the belt 16 and the motor 18 are arranged on a support cross-member 20 attached through articulated hinge elements 21 to the bearing structure 15 of the device 11 of the invention. The pulleys 17 are indeed rotatably carried on the cross-member 20.

Furthermore, the cross-member 20 carries an integral lever 22 which is connected in an articulated manner through a pin 23 to the end of a stem 24 of an actuating cylinder 25, attached through a pin 26 to the aforementioned bearing structure 15.

Consequently, thanks to the aforementioned general structure, the cross-member 20 and therefore the manipulators 19, 19' carried on it can oscillate according to the arrow F to determine both the gripping of the individual product 12 from the first conveyor belt 13 and the subsequent laying down thereof on the second conveyor belt 14. This takes place both for the manipulator 19 arranged on a side of the cross-member 20 and for the other manipulator 19' arranged on the other side of the cross-member 20. In this way the device of the present invention allows the two manipulators 19, 19' to be carried, always in two preselected positions with respect to both the first conveyor belt 13 and the second conveyor belt 14, in other words gripping and laying down the individual product always in the same positions.

The individual manipulator 19, 19' foresees a series of cylinders 27 arranged on a plate 28 connected to a bracket 29 made integral with the belt 16 through bolts 30. The cylinders 27 through their stems 31 carry first gripping members, such as suction pads 32, which act upon the individual publishing product 12.

The presence of the series of cylinders 27, in which each cylinder 27 foresees an adaptation to each gripped publishing product 12, allows adaptation of the individual manipulator 19, 19' to the publishing product 12 so that the product itself can even have a variable thickness from one point to the next. The pistons 31 of these cylinders 27 are thus self-levelling and self-adapting.

Moreover, each manipulator 19 and 19' is also equipped with a square-shaped element 33, hinged at 34 to the plate 28, an end of which is hinged at 35 to an end of a stem of a cylinder 36. This cylinder 36 is in turn hinged at the other end at 37 to the aforementioned plate 28 and determines the actuation of the square-shaped element 33 which functions as a second gripping member.

This square-shaped element 33 is thus actuated to grip the publishing product 12 in its lower part so as to act in collaboration with the suction pads 32 of the cylinders 27 like a pincer and to realise complete and secure gripping members.

For greater certainty of placing of the publishing products 12 separated one after the next on the second conveyor belt 14, said conveyor belt 14 can be arranged tilted by a certain angle with respect to the first conveyor belt 13, for example about 45°. In this way, as shown in the figures, the placing of the publishing products 11 being discharged, to be sent to subsequent selection, sorting and type and origin checking operations of leftover publishing products, is made even more certain. Indeed, in this way it is certain that the products shall not be arranged scaled as happened on the first transporter.

As can be observed from the figures, such an angled arrangement of the products 12 ensures that the product does not open, if folded like a magazine. Moreover, the presence of barcodes 40 arranged both on the upper and lower side allows correct and easy reading with normal scanners, schematised at 38, arranged at 45° in the upper part of the apparatus or else with a scanner just in the upper or lower part 39 arranged transversally to the direction of travel.

In particular, in the operation given as an example, the device as shown in FIG. 1 is oscillated so that a manipulator 19 is in the step of gripping an publishing product 12 arranged on the first conveyor belt 13. The series of cylinders 27 arranged on the plate 28 through the respective stems 31 has carried the first gripping members, i.e. the suction pads 32, onto the first publishing product 12 of the products arranged scaled on the first conveyor belt 13.

The second manipulator 19', on the other hand, having released another publishing product 12 on the second conveyor belt 14, is carried by such an oscillation far from the second conveyor belt 14.

In a subsequent step the manipulator 19 is carried above the second conveyor belt 14, whereas the manipulator 19' is carried above the first conveyor belt 13. Such a displacement is determined by the translation of the belt 16 actuated by pulleys 17. In such a way the publishing product 12 (F) gripped by the manipulator 19 is carried onto the second conveyor belt 14 and is released distanced and separated from the previous product 12 (FIG. 2).

Immediately after such an operation the cross-member 20 is made to oscillate by the cylinder 25 which pulls back the stem 24. In such a way the manipulator 19' goes above a further product 12 arranged on the first conveyor belt 13, whereas the other manipulator 19 moves away from the product 12 released on the second conveyor belt 14. The manipulator 19' is made to translate until the product 12 is laid down on the second conveyor belt 14, as shown in FIG. 3.

It must be specified that during the gripping operation the further gripping member defined by the square-shaped element 33 also enters into action. Indeed, the cylinder 36 determines the oscillation of the square-shaped element 33 which goes below the publishing product 12 and acts in collaboration with the suction pads 32 of the cylinders 27 like a pincer on the product 12.

The complete cycle is then repeated to also carry this further publishing product, which arrives arranged scaled, towards an individual arrangement on the second conveyor belt 14, certainly "individualised" and ready to make the carrying out of the successive selection, sorting and type and origin check operations of leftover publishing products as automatic and fast as possible.

It is thus clear how simple and useful a solution to the general problem mentioned previously, according to the present invention, has been found to be.

The proposed technical solution realises the possibility of individual positioning of the publishing product which arrives overlapping.

What is claimed is:

1. Automatic feed device for separating individual publishing products of varying thickness and size, comprising a first conveyer belt (13) and a second conveyor belt (14) in a scaled arrangement, the first conveyor belt (13) being partially on top of the second conveyor belt (14) said automatic feed device comprising a bearing structure (15), at least one pair of manipulator members (19) which, one at a time, grip, through relative gripping members (27, 32, 33), the publishing products (12), on the first conveyor belt (13) and thereafter lay down said publishing products (12) on the second conveyor belt (14) separate from one another, said manipulators (19) being alternately mobile forwards and backwards between said first and second conveyor belts (13, 14) and being able to oscillate to determine both the gripping of the individual publishing products (12) and the subsequent laying down thereof of said publishing products (12) in two predetermined positions on said first and second conveyor belts (13,14).

2. Device according to claim 1, wherein said second conveyor belt (14) and at least one upper and/or lower scanner (38, 39) of barcodes (40), arranged on each of said publishing products (12) separated from one another, is associated.

3. Device according to claim 1, wherein said manipulators (19) are arranged on a cross-member (20) which can oscillate with respect to said bearing structure (15) through an actuator (25) and relative articulations (21, 22, 23, 26) said manipulators (19) being alternately mobile forwards and backwards along said cross-member (20) through an actuator arrangement (16, 17, 18).

4. Device according to claim 3, wherein said articulations (21, 22, 23, 26) comprise articulated hinged elements (21) arranged between said support cross-member (20) and said bearing structure (15) and, respectively, a lever (22) integral with said cross-member (20) and connected in an articulated manner through a pin (23) to said actuator consisting of cylinder (25), attached through a pin (26) to said bearing structure (15).

5. Device according to claim 3, wherein said actuator arrangement comprises a belt (16) wound into a ring on end pulleys (17), rotatably mounted on said cross-member (20), one of said pulleys (17) being connected to a motor means (18) which moves in and alternating forward and backward motion.

6. Device according to claim 5, including motor means which comprises a brushless motor (18) or an electric shaft group.

7. Device according to claim 3 or 5 wherein each of said at least one pair of manipulator members (19) comprise gripping members which comprise a series of cylinders (27), carrying suction pads (32) which act on said publishing products (12), said cylinders (27) being arranged on a plate (28) which is mobile with respect to said cross-member (20).

8. Device according to claim 7, wherein said gripping members also comprise a square-shaped element (33), hinged (at 34) to said plate (28), one end of which is hinged (at 35) to an end of a stem of a cylinder (36) which in turn is hinged at the other end (at 37) to said plate (28).

9. Device according to claim 7, wherein said series of cylinders (27), carrying suction pads (32), are adapted to be self-leveling with respect to each publishing product (12) being gripped.

10. Device according to claim 7, wherein each of said at least one pair of manipulator members (19) is mobile on one side of said cross-member (20) forwards and backwards.

* * * * *